US00PP33158P3

(12) United States Plant Patent
Pineau

(10) Patent No.: US PP33,158 P3
(45) Date of Patent: Jun. 15, 2021

(54) ***POTENTILLA* PLANT NAMED 'MINCRERO01'**

(50) Latin Name: *Potentilla fruticosa*
Varietal Denomination: Mincrero01

(71) Applicant: HORTIVAL DIFFUSION SAS, Beaufort en Anjou (FR)

(72) Inventor: Patrick Pineau, Saint Mathurin sur Loire (FR)

(73) Assignee: HORTIVAL DIFFUSION SAS, Beaufort en Anjou (FR)

( * ) Notice: Subject to any disclaimer, the term of this patent is extended or adjusted under 35 U.S.C. 154(b) by 0 days.

(21) Appl. No.: 16/905,058

(22) Filed: Jun. 18, 2020

(65) Prior Publication Data

US 2020/0404825 P1 Dec. 24, 2020

(30) Foreign Application Priority Data

Jun. 20, 2019 (QZ) ..... PBR 2019/1500

(51) Int. Cl.
*A01H 6/74* (2018.01)
*A01H 5/02* (2018.01)
*A01H 6/00* (2018.01)

(52) U.S. Cl.
USPC ..... Plt./237
CPC ..... *A01H 6/00* (2018.05); *A01H 5/02* (2013.01)

(58) Field of Classification Search
USPC ..... Plt./237
See application file for complete search history.

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct cultivar of *Potentilla* plant named 'Mincrero01' is disclosed. The new variety is characterized by exhibiting semi-double cream colored flowers tinted with pink, forming medium green colored foliage, and exhibiting moderately vigorous compact and bushy growth habit. The new variety is particularly well suited for providing distinctive ornamentation in the landscape.

2 Drawing Sheets

Figure 1:
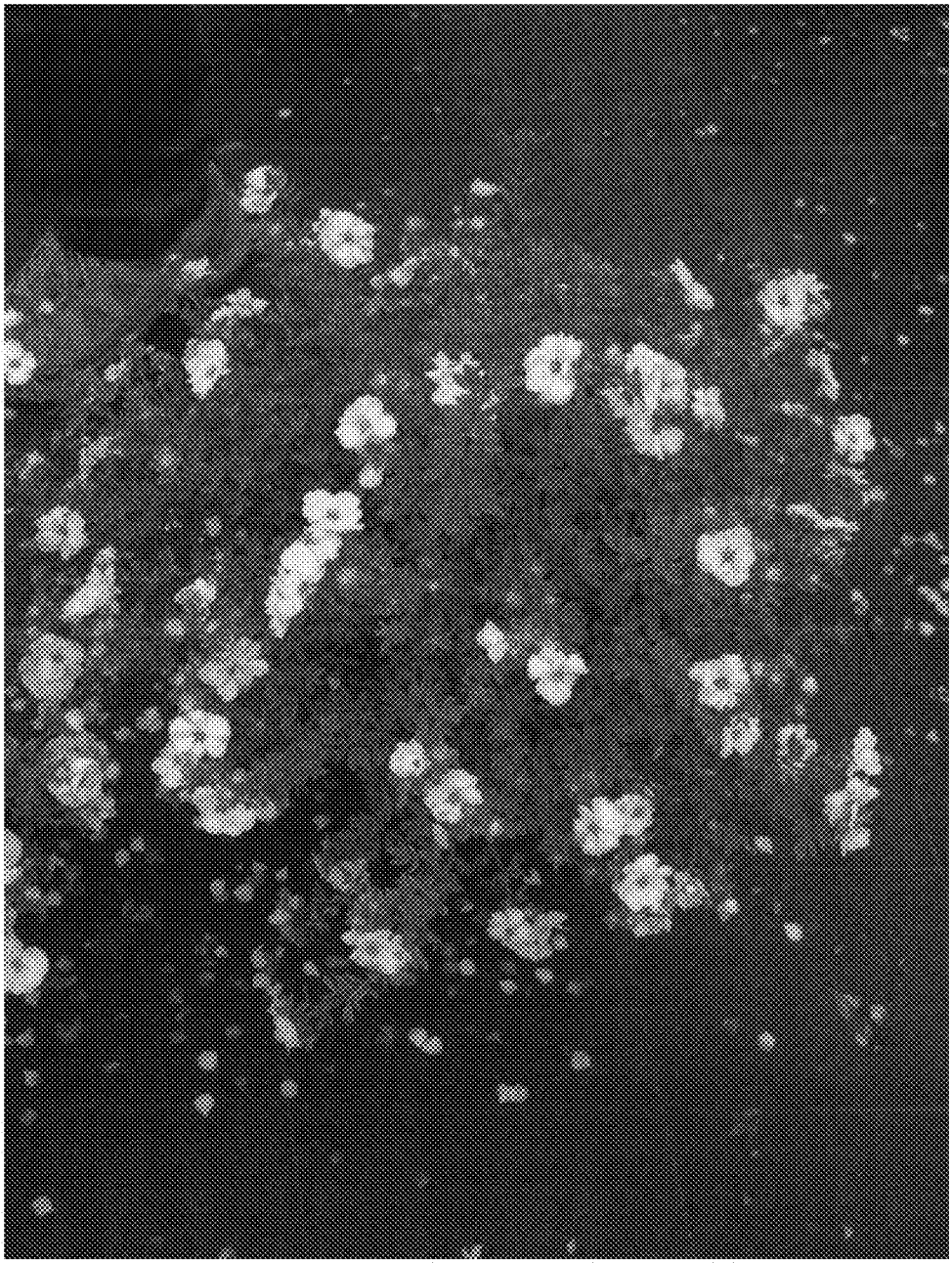

Latin name of genus and species of plant claimed: *Potentilla fruticosa.*

Variety denomination: 'Mincrecro01'.

CROSS-REFERENCE TO RELATED APPLICATIONS

This application claims priority to Plant Breeders' Right Application Number 2019/1500, which was filed at Community Plant Variety Office in the European Union on Jun. 20, 2019, the contents of which are hereby incorporated by reference for all purposes.

BACKGROUND OF THE INVENTION

The present invention relates to a new and distinct cultivar of *Potentilla* plant botanically known as *Potentilla fruticosa* and hereinafter referred to by the cultivar name 'Mincrero01'.

The new cultivar originated in a controlled breeding program in La Menitre, Maine Et Loire, France, during July 2009. The objective of the breeding program was to develop double flowers in the *Potentilla* genus.

The new cultivar was discovered in La Menitre, Maine Et Loire, France. The new *Potentilla* cultivar is the result of cross-pollination. The female (seed) parent of the new cultivar is an unnamed breeder seedling, (not patented), characterized by its semi double yellow flowers, yellow and red flower buds, and moderate compact growth habit. The male (pollen) parent of the new cultivar is an unnamed breeder seedling (not patented), characterized by its semi-double pink colored flowers and compact growth habit.

The new cultivar was discovered and selected as a single flowering plant within the progeny of the above stated cross-pollination during September 2011 in a controlled environment in La Menitre, Maine Et Loire, France.

Asexual reproduction of the new cultivar by softwood cuttings since September 2011 in La Menitre, Maine Et Loire, France has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Mincrero01' as a new and distinct cultivar of *Potentilla* plant:

(a) forms semi-double cream colored flowers tinted with pink,
(b) exhibits medium green colored foliage, and
(c) provides moderately vigorous, compact and bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the female parent (i.e., the seed parent) displays yellow colored flowers and yellow and red colored flower buds, and exhibits a moderate compact growth habit, whereas the new variety displays cream colored flowers tinted with pink and cream and pink colored flower buds, and exhibits a more rounded growth habit compared to the female parent. The male parent (i.e., the pollen parent) displays pink colored flowers, whereas the new variety displays cream colored flowers tinted with pink and a more rounded growth habit compared to the male parent.

Moreover, the new variety can be readily distinguished from other similar non-parental varieties. Of the many commercially available *Potentilla* cultivars, the most similar in comparison to the new cultivar is *Potentilla* 'Snowbird' (not patented). However, plants of 'Snowbird' exhibit a less compact growth habit and lower petal count compared to the new variety.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of the new variety. The illustrated plants of the new variety were grown in 4-liter containers for two years in an outdoor nursery in La Menitre, Maine Et Loire, France.

FIG. 1—illustrates a specimen of the plant—side view of the overall growth and flowering habit.

Figure 2:
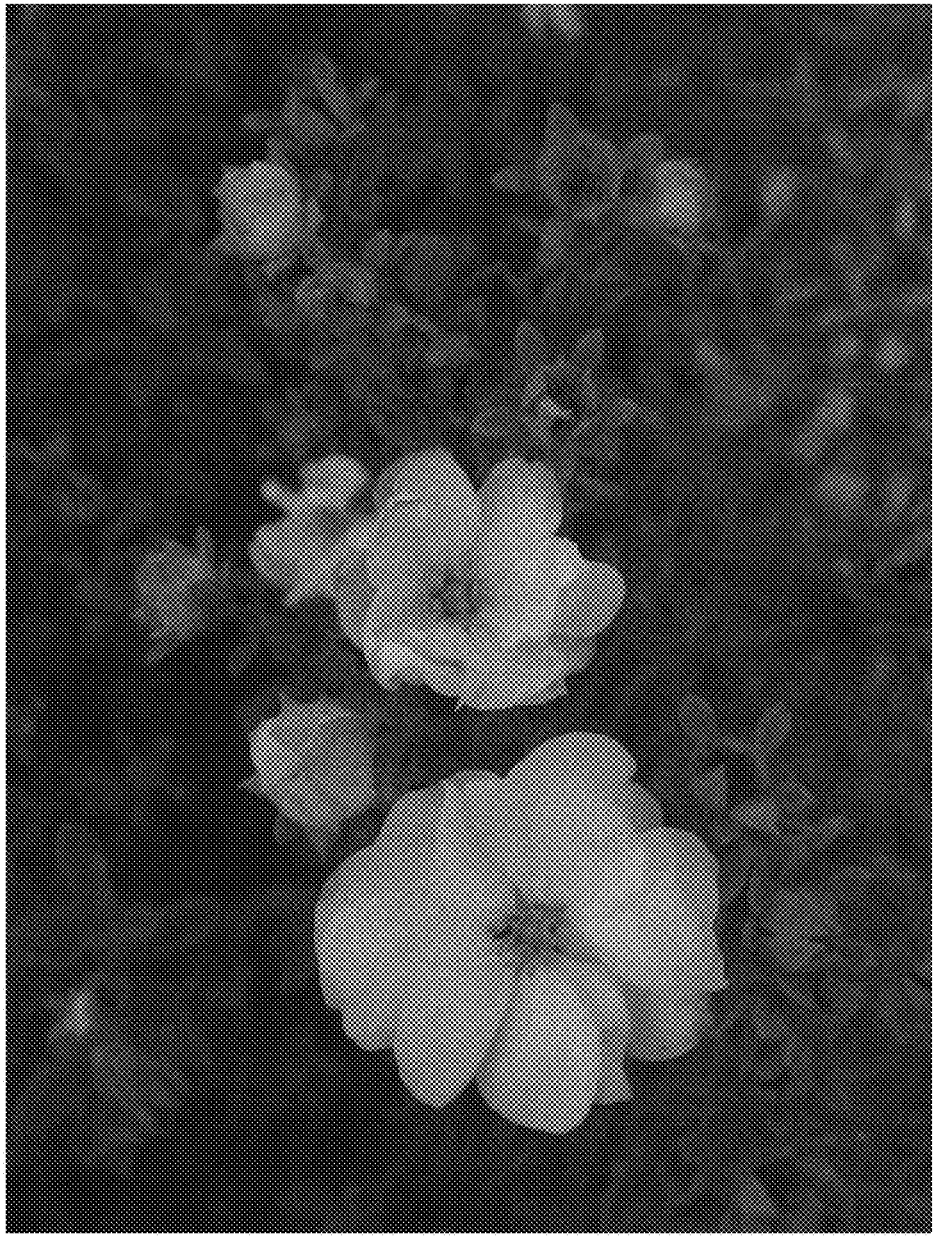

FIG. 2—illustrates a specimen of a flower cluster—close-up view.

DETAILED BOTANICAL DESCRIPTION

The chart used in the identification of colors described herein is that of The Royal Horticultural Society (R.H.S. Colour Chart), London, England, 2001 edition, except where general color terms of ordinary significance are used. The terminology which precedes reference to the chart has been added to indicate the corresponding color in more common terms. The color values were determined in June 2019 under natural light conditions in La Menitre, Maine Et Loire, France.

The following descriptions, including measurements, is based on the observation of specimens of the new variety during 2020 produced from cuttings from stock plants and grown in 17.0 cm containers for approximately 15 months in an outdoor nursery in La Menitre, Maine Et Loire, France. Plants were pinched once after transplant.

Botanical classification: *Potentilla fruticosa* cultivar Mincrero01.

Parentage:

*Female parent*.—Unnamed breeder seedling, not patented.

*Male parent*.—Unnamed breeder seedling, not patented.

Propagation:

*Type cutting*.—Stem cutting.

*Time to initiate roots*.—Approximately 40 to 60 days.

*Time to produce a rooted cutting*.—Approximately 80 to 100 days.

*Root description*.—Fibrous.

*Rooting habit*.—Freely branching.

Plant description:

*Commercial crop time*.—Approximately 36 months from a rooted cutting to finish in 17.0 cm container.

*Growth habit and general appearance*.—Moderately vigorous, compact and bushy growth habit.

*Size*.—Height from soil level to top of plant plane: approximately 23.0 cm on average. Width: approximately 23.0 cm on average.

*Branching habit*.—Freely branching, pinching enhances basal branching. Quantity of main branches per plant: approximately 47 on average.

*Branch*.—Strength: strong, somewhat flexible, becomes woody with age. Length: approximately 18.0 cm on average. Diameter: approximately 4.0 mm on average. Length of central internode: approximately 1.3 cm on average. Texture: pubescent. Color of young stems: commonly near Greyed-Orange Group 176A. Color of mature stems: commonly near Brown Group 200C.

Foliage description:

*General description*.—Quantity of leaves per branch: approximately 22 on average. Quantity of leaves per branched lateral stem: approximately 12 on average. Fragrance: none detected. Form: palmately compound, 3 to 5 leaflets present. Arrangement: alternate. Durability to stress: moderate to high.

*Leaves*.—Aspect: primarily perpendicular to stem. Shape: oblong. Margin: entire. Apex: obtuse. Base: acute. Venation pattern: pinnate and inconspicuous. Length of mature leaf: approximately 2.0 cm on average. Width of mature leaf: approximately 2.5 cm on average. Texture of upper and lower surfaces: pubescent. Color of upper surface of mature foliage: commonly near Green Group 138A. Color of lower surface of mature foliage: commonly near Green Group 138B.

*Petiole*.—Shape: orbicular. Length: approximately 5.0 mm on average. Width: approximately 1.0 mm on average. Texture: pubescent. Color: commonly near Yellow-Green Group 145B.

Flowering description:

*Flowering habit*.—Freely flowering under outdoor growing conditions with substantially continuous blooming from late spring through mid-fall.

*Lastingness of individual flower*.—Approximately 5 days. Self-cleaning.

Inflorescence description:

*General description*.—Type: solitary, axillary at the apex of stems. Quantity of open inflorescences per plant: approximately 77 on average. Fragrance: none.

Flower description:

*Type*.—Semi-double.

*Bud just before opening*.—Shape: flattened globose. Length: approximately 7.0 mm on average. Diameter: approximately 6.0 mm on average. Texture: soft. Color of petals: commonly near Yellow Group 4D and Red Group 48A.

*Corolla*.—Shape: rotate. Depth: approximately 0.5 cm on average. Diameter: approximately 3.0 cm on average.

*Petals*.—Shape: obovate to orbicular. Margin: entire. Apex: orbicular. Length: approximately 13.0 mm on average. Width: approximately 12.0 mm on average. Texture of upper and lower surfaces: soft, smooth.

Color of upper and lower surfaces when first and fully open: commonly near Yellow Group 2D with commonly near Red Group 48B on the outer petals. Number of petals: approximately 13 to 15 per flower.

*Calyx*.—Shape: bowl, convex base. Length: approximately 2.0 mm. Diameter: approximately 4.0 mm.

*Sepals*.—Quantity per flower: 5. Apex: acute. Margin: entire. Length: approximately 5.0 mm on average. Width: approximately 3.0 mm on average. Texture of inner surface: pubescent. Texture of outer surface: pubescent. Color of inner and outer surfaces: commonly near Yellow-Green Group 145B with commonly near Greyed-Red Group 179A.

*Pedicels*.—Strength: good. Length: approximately 8.0 mm on average. Diameter: Approximately 1.0 mm on average. Texture: pubescent. Color: commonly near Yellow-Green Group 145B with near Greyed-Red Group 179A.

*Reproductive organs*.—Androecium: Stamen quantity: approximately 19 per flower. Anther shape: cordate. Anther length: approximately 2.0 mm. Anther color: commonly near Yellow-Orange Group 15A. Pollen amount: scarce. Pollen color: commonly near Yellow-Orange Group 15A. Gynoecium: Pistil quantity: approximately 25 per flower. Pistil length: approximately 2.0 mm on average. Stigma shape: capitate. Stigma length: approximately 1.0 mm on average. Stigma color: commonly near Yellow Group 2A. Style length: approximately 2.0 mm on average. Style color: commonly near Yellow Group 2A. Ovary length: approximately 0.5 mm on average. Ovary color: commonly near Yellow-Green Group 145A.

Development:

*Seed and fruit production*.—Not observed to date.

*Disease and pest resistance*.—Resistance to pathogens and pests common to *Potentilla* has not been observed.

Plants of 'Mincrero01' have not been observed under all possible environmental conditions to date. Accordingly, it is possible that the phenotypic expression may vary somewhat with variations in the environment, such as temperature, light intensity, and day length, without, however, any variance in genotype.

I claim:

1. A new and distinct *Potentilla* plant characterized by the following combination of characteristics:

(a) forms semi-double cream colored flowers tinted with pink, (b) exhibits medium green colored foliage, and (c) provides moderately vigorous, compact and bushy growth habit;

substantially as herein shown and described.

* * * * *